United States Patent
Wang

(10) Patent No.: US 12,297,244 B2
(45) Date of Patent: May 13, 2025

(54) SYSTEMS AND METHODS FOR INHIBITING γ-SECRETASE PRODUCTION OF AMYLOID-β PEPTIDES

(71) Applicant: Rensselaer Polytechnic Institute, Troy, NY (US)

(72) Inventor: Chunyu Wang, Latham, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 630 days.

(21) Appl. No.: 17/352,620

(22) Filed: Jun. 21, 2021

(65) Prior Publication Data

US 2021/0309705 A1    Oct. 7, 2021

Related U.S. Application Data

(63) Continuation-in-part of application No. PCT/US2020/036244, filed on Jun. 5, 2020.

(60) Provisional application No. 63/041,873, filed on Jun. 20, 2020.

(51) Int. Cl.
| | |
|---|---|
| *A61K 38/00* | (2006.01) |
| *C07K 14/47* | (2006.01) |
| *C12N 9/64* | (2006.01) |

(52) U.S. Cl.
CPC ........ *C07K 14/4711* (2013.01); *C12N 9/6478* (2013.01); *A61K 38/00* (2013.01); *C07K 2319/03* (2013.01)

(58) Field of Classification Search
CPC ............ C07K 14/4711; C07K 2319/03; C12N 9/6478; A61K 38/00
See application file for complete search history.

(56) References Cited

U.S. PATENT DOCUMENTS

| | | | |
|---|---|---|---|
| 6,717,031 B2 | 4/2004 | Games et al. | |
| 6,794,363 B2 | 9/2004 | Bejanin et al. | |
| 6,844,148 B1 | 1/2005 | Gurney et al. | |
| 7,041,473 B1 | 5/2006 | Gurney et al. | |
| 7,045,531 B1 | 5/2006 | Bush et al. | |
| 7,183,070 B2 | 2/2007 | Cordell et al. | |
| 7,252,963 B2 | 8/2007 | Anderson et al. | |
| 7,456,007 B1 | 11/2008 | Anderson et al. | |
| 7,910,586 B2 | 3/2011 | Netzer et al. | |
| 8,147,833 B2 | 4/2012 | Schenk et al. | |
| 8,598,171 B2 | 12/2013 | Netzer et al. | |
| 8,691,864 B2 | 4/2014 | Greig et al. | |
| 9,539,235 B2 | 1/2017 | Etcheberrigaray et al. | |
| 9,650,336 B2 | 5/2017 | Minidis et al. | |
| 9,707,231 B2 | 7/2017 | Sutcliffe et al. | |
| 9,725,469 B2 | 8/2017 | White et al. | |
| 9,777,019 B2 | 10/2017 | White et al. | |
| 9,834,559 B2 | 12/2017 | Oehlrich et al. | |
| 9,949,975 B2 | 4/2018 | Bukhtiyarov et al. | |
| 2006/0063717 A1 | 3/2006 | Boyd et al. | |
| 2006/0281699 A1 | 12/2006 | Merchiers et al. | |
| 2016/0129002 A1 | 5/2016 | Besidski et al. | |
| 2016/0158242 A1 | 6/2016 | Kroth et al. | |

FOREIGN PATENT DOCUMENTS

WO    WO-2005063796 A1 *  7/2005  ......... C07K 14/4711

OTHER PUBLICATIONS

International Search Report and the Written Opinion of the International Searching Authority, International Application No. PCT/US2020/036244, mailed Sep. 3, 2020.
Shelton, C.C., et al., "Modulation of gamma—secretase specificity using small molecule allosteric inhibitors," PNAS, vol. 106, No. 48, pp. 20228-20233, Dec. 1, 2009.
Tian, G., et al., "The Mechanism of gamma-Secretase," The Journal of Biological Chemistry, vol. 278, No. 31, pp. 28968-28975, Apr. 28, 2003.
Zhao, J., et al., "Substrate interaction inhibits gamma-secretase production of amyloid-beta peptides," Chemical Communications, vol. 56, pp. 2578-2581, Feb. 3, 2020.

* cited by examiner

*Primary Examiner* — Jeanette M Lieb
(74) *Attorney, Agent, or Firm* — Barclay Damon LLP; Anthony P. Gangemi

(57) ABSTRACT

Inhibitors are provided for targeting γ-secretase to reduce amyloid load as a viable strategy in Alzheimer's disease treatment and drug discovery. γ-secretase has been shown to cleave amyloid precursor protein, causing an increase in extracellular concentration of amyloid-β peptides. This extracellular concentration increase can lead to build-up amyloid plaques in patients and associated health complications for them. The inhibitors bind to a C-terminal lysine cluster adjacent the transmembrane domain of amyloid precursor protein through both covalent and non-covalent interactions. These interactions inhibit the ability of γ-secretase to cleave the amyloid precursor protein, halting the build-up of extracellular amyloid-β peptides. The inhibitors exhibit specificity for amyloid precursor proteins, reducing concerns of potential off-target effects.

20 Claims, 12 Drawing Sheets

| No. | Comp. ID | Structure |
|---|---|---|
| 1 | 19-148-203 | 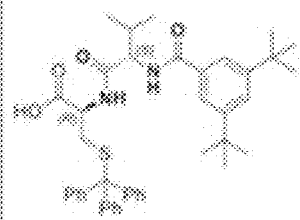 |
| 2 | 33-148-203 | 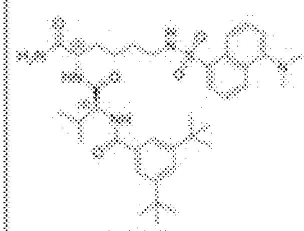 |
| 3 | 175-148-203 | 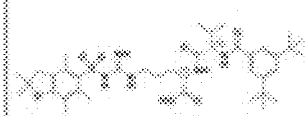 |
| 4 | 175-134-306 | 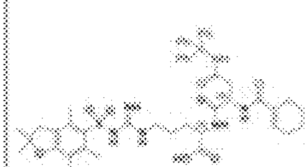 |

SYSTEMS AND METHODS FOR INHIBITING γ-SECRETASE PRODUCTION OF AMYLOID-β PEPTIDES

CROSS REFERENCE TO RELATED APPLICATION(S)

This application is a continuation-in-part of International Patent Application No. PCT/US2020/036244, filed Jun. 5, 2020, which claims the benefit of U.S. Provisional Application No. 62/857,513, filed Jun. 5, 2019, and this application further claims the benefit of U.S. Provisional Application No. 63/041,873, filed Jun. 20, 2020, which are incorporated by reference as if disclosed herein in their entireties.

BACKGROUND

In intramembrane proteolysis (IP), an integral membrane protein is cleaved by intramembrane cleaving proteases (I-CLiPs) within the transmembrane domain (TM) to liberate biologically active fragments. As a unique form of signal transduction, I-CLiPs play essential roles in numerous physiological processes such as embryonic development, immune responses, and normal function of the nervous system.

I-CLiPs also play crucial roles in physiological and pathological processes, such as Alzheimer's disease and cancer. However, the mechanisms of substrate recognition by I-CLiPs remain poorly understood. The aspartic I-CLiP presenilin is the catalytic subunit of the γ-secretase complex, which releases amyloid-β peptides (Aβs) through intramembrane proteolysis of the transmembrane domain of the amyloid precursor protein (APPTM). γ-secretase is a transmembrane protein complex whose catalytic component is the presenilin protein which harbors the active site aspartates. Mutations in presenilin and APP (such as V44M in APPTM) can cause familial AD (FAD) characterized by early onset of dementia and increased Aβ42/Aβ40 ratio.

Unlike soluble proteases which recognize specific amino acid sequences, I-CLiPs display promiscuity against transmembrane substrates. To date, over 90 physiological substrates, e.g., Notch, are known for presenilin/γ-secretase, with no apparent consensus recognition motif. Substrate promiscuity of γ-secretase has contributed to the failure of clinical trials of γ-secretase inhibitors, e.g., through the inhibition of the Notch signaling pathway. Thus understanding substrate/enzyme interaction in I-CLiPs will not only contribute to fundamental understanding of I-CLiPs but also may provide novel insights for selective inhibition of γ-secretase in Alzheimer's disease drug discovery.

Alzheimer's disease (AD) is a progressive neurodegenerative disorder responsible for an increasing number of cases of dementia in the elderly. Without a disease-modifying therapy, there is a pressing need to develop novel and more efficient therapeutic strategies to delay and/or prevent AD occurrence. The neuropathological hallmarks of AD include the presence of senile plaques in the cerebral cortex and hippocampus. These plaques, which are mainly composed of extracellular aggregates of amyloid β-peptides, have been hypothesized to initiate a pathological cascade that results in cognitive decline.

γ-secretase is a promising drug target for reducing amyloid load. γ-Secretase is an aspartyl intramembrane protease, composed of at least four essential proteins, presenilin (PS), nicastrin (Nct), anterior pharynx-defective 1 (Aph-1), and presenilin enhancer 2 (Pen-2), among which PS is the catalytic subunit. Most of the FAD mutations occur within PS genes. Because there are the two isoforms of PS (PS1 and PS2) with distinct substrate specificities and two isoforms of Aph1, there exists at least four major forms of the γ-secretase complexes, with alternative splicing generating even more variant forms of γ-secretase. Thus, γ-secretase is effectively a group of proteases with different subunit compositions and diverse cleavage specificity, as it has been shown that several substrates are cleaved by PS1-containing γ-secretase complex but not by PS2-containing γ-secretase complex. The specific functions of each form of γ-secretase are not known, contributing to the uncertainty in the possible side effects of broad spectrum γ-secretase inhibition. An even more significant obstacle for the development of γ-secretase inhibitors as drug candidates is the large number of substrates of γ-secretase, with over 90 reported to date.

Despite intense effort, clinical trials of anti-Aβ drugs have so far failed. Clinical trials of γ-secretase inhibitors have failed due to serious side effects which may be attributed to the suppression of γ-secretase activity against other substrates, such as Notch, N-cadherin, and tyrosinase. Two broad spectrum γ-secretase inhibitors, avagacestat and semagacestat, failed due to serious adverse effects and worsening cognition in patients. In addition, γ-secretase inhibitors bind directly to PS, the catalytic subunit of γ-secretase. PS is involved in learning and memory, and neuronal survival during aging. PS inhibition by γ-secretase inhibitors has been predicted to result in the accumulation of potentially toxic uncleaved transmembrane substrates of γ-substrate and may have contributed to the declining cognitive ability seen in clinical trials.

Because APPTM is the substrate for γ-secretase to generate AD, an alternative and unexplored approach is to target the substrate APPTM instead of γ-secretase to reduce Aβ production. A substrate-specific inhibitor is not expected to affect the γ-secretase cleavage of other physiological substrates, the assembly of the γ-secretase complex, or any presenilin function, thereby sparing the side effects associated with broad-spectrum γ-secretase inhibitors.

Several compounds have been reported to bind to APP and inhibit Aβ production, but it is not clear whether they directly bind to APPTM to exert their effects. Although γ-secretase modulators (GSMs, such as fenofibrate and tarenflurbil) were initially reported to bind to APPTM, no specific binding between GSM and APPTM was found in further studies. The anti-cancer drug bexarotene can reduce amyloid load and alleviate neurodegeneration, but a recent study showed that bexarotene inhibits γ-secretase with low efficacy and this effect is not due to substrate binding.

A major concern for covalent modifiers is its non-specificity and off-target reactivity. Although the pharmaceutical industry traditionally avoids drugs that form covalent bonds with their targets, many first-in-class drugs, such as aspirin, penicillin, and esomeprazole, function through a covalent mechanism and make up about 30% of the drug market. Covalent drugs are indeed a highly effective class of therapeutics with the advantages of high efficacy, due to the zero off-rate. This enables lower dosage and less frequency dosing, which mitigates side effects and off-target effects, and increases compliance. In recent years, covalent compounds have seen a resurgence in drug discovery, with many covalent candidates in drug development pipeline. In particular, covalent compounds can be used to address "undruggable" targets with shallow surfaces and no obvious binding pockets.

SUMMARY

Some embodiments of the present disclosure are directed to an inhibitor of γ-secretase cleavage of amyloid precursor protein. In some embodiments, the inhibitor includes a structure including:

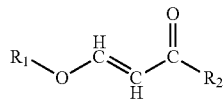

(Formula I)

wherein $R_1$ includes one or more aryl groups, heterocyclic groups, $C_{7-10}$ hydrocarbyl groups, or combinations thereof, and $R_2$ includes one or more aryl groups, heterocyclic groups, $C_{7-10}$ hydrocarbyl groups, or combinations thereof. In some embodiments, $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, the structure includes:

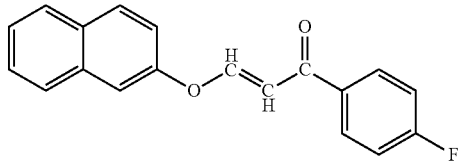

(Formula III)

Some embodiments of the present disclosure are directed to a method for inhibiting γ-secretase cleavage of amyloid precursor protein including providing a composition including a pharmaceutically effective amount of a structure configured to bind to a domain of an amyloid precursor protein, providing the composition to the domain, and binding the structure to the domain. In some embodiments, the composition includes a pharmaceutically acceptable buffer, diluent, carrier, adjuvant, excipient, or combinations thereof. In some embodiments, the domain includes an amyloid precursor protein transmembrane domain, amyloid precursor protein juxtamembrane region, or combinations thereof. In some embodiments, binding the structure to the domain includes modifying one or more lysine residues of a C-terminal juxtamembrane region adjacent a transmembrane domain. In some embodiments, binding the structure to the domain includes covalent and non-covalent binding. In some embodiments, the concentration of the structure in an environment surrounding the domain after providing the composition is about 25 μM.

In some embodiments of the method, the structure includes:

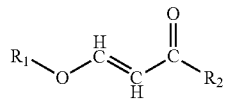

(Formula I)

wherein $R_1$ includes one or more aryl groups, heterocyclic groups, $C_{7-10}$ hydrocarbyl groups, or combinations thereof, and $R_2$ includes one or more aryl groups, heterocyclic groups, $C_{7-10}$ hydrocarbyl groups, or combinations thereof. In some embodiments, $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof.

Some embodiments of the present disclosure are directed to a method of reducing an amyloid load in a patient to treat a disease including identifying a presence of extracellular aggregates of amyloid-β peptides in the patient, and administering an effective amount of a composition including a structure including:

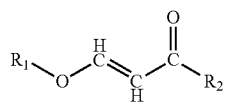

(Formula I)

In some embodiments, $R_1$ includes one or more aryl groups, heterocyclic groups, $C_{7-10}$ hydrocarbyl groups, or combinations thereof, and $R_2$ includes one or more aryl groups, heterocyclic groups, $C_{7-10}$ hydrocarbyl groups, or combinations thereof. In some embodiments, $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, the composition includes a pharmaceutically acceptable buffer, diluent, carrier, adjuvant, excipient, or combinations thereof. In some embodiments, the method includes binding the structure to a domain of an amyloid precursor protein, wherein the domain includes an amyloid precursor protein transmembrane domain, amyloid precursor protein juxtamembrane region, or combinations thereof. In some embodiments, the concentration of the structure in an environment surrounding the domain of amyloid precursor protein after providing the composition is about 25 μM. In some embodiments, the disease is Alzheimer's disease.

In some embodiments of the method, binding the structure to the domain includes modifying one or more lysine residues of a C-terminal juxtamembrane region adjacent a transmembrane domain. In some embodiments, binding the structure to the domain includes covalent and non-covalent binding.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DESCRIPTION

Figure 1:
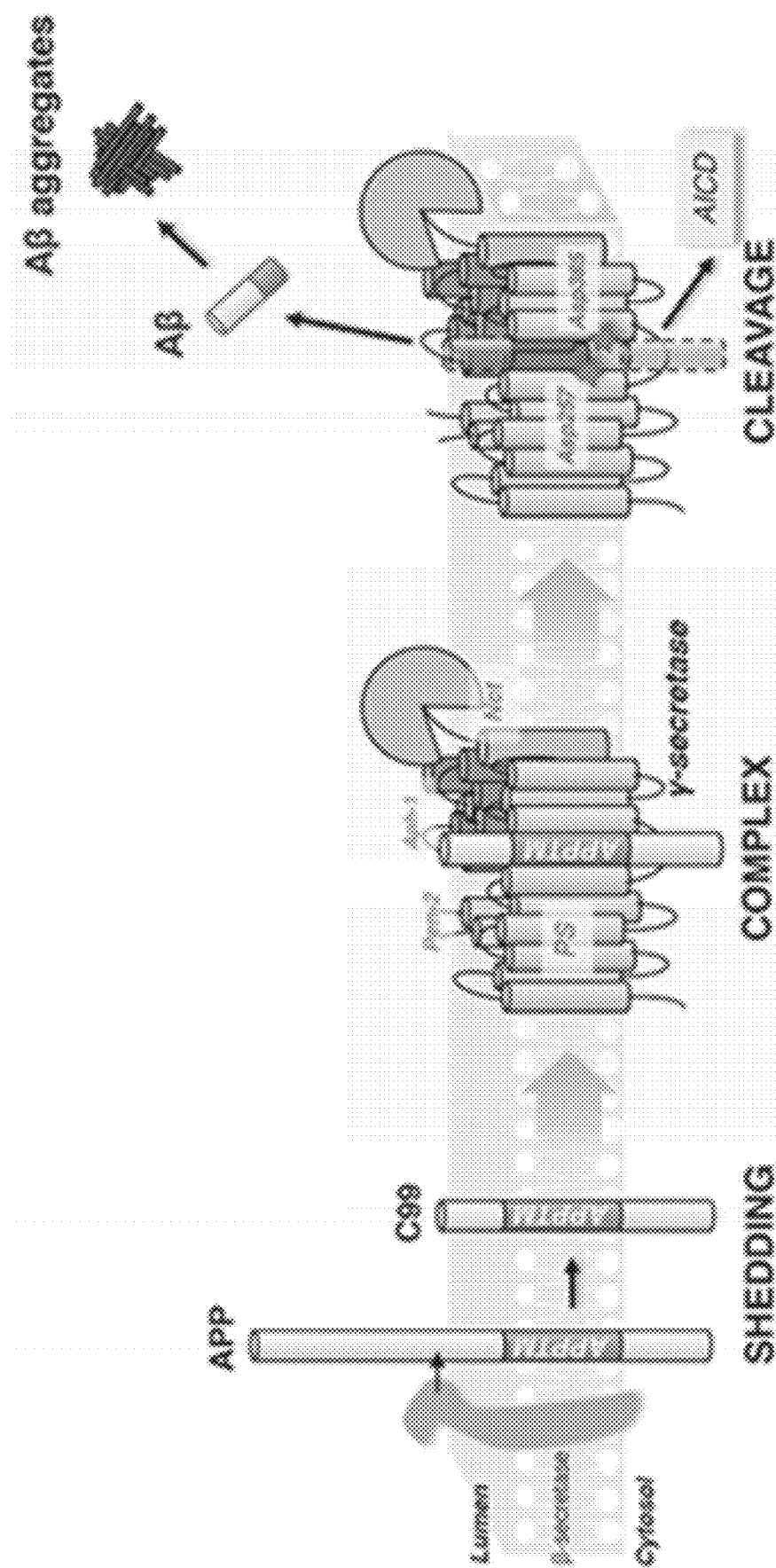
FIG. 1 is a schematic representation of γ-secretase cleavage that is inhibited by inhibitors according to some embodiments of the present disclosure.

Some embodiments of the present disclosure are directed to an inhibitor of γ-secretase cleavage of amyloid precursor protein. In some embodiments, the inhibitor includes a structure according to the following Formula I:

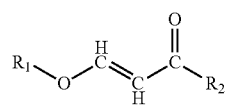

(Formula I)

In some embodiments, $R_1$ includes one or more aryl groups, heterocyclic groups, $C_{7-10}$ hydrocarbyl groups, or combinations thereof. In some embodiments, $R_2$ includes one or more aryl groups, heterocyclic groups, $C_{7-10}$ hydrocarbyl groups, or combinations thereof. As used herein, the term "hydrocarbyl" is used to refer to branched linear, unbranched linear, and cyclic structures of carbon and hydrogen atoms, including saturated, unsaturated, substituted, and unsubstituted forms, as well as forms including one or more of N, O, or S, or combinations thereof. In some embodiments, $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_1$ and $R_2$ are separated by a linker region. In some embodiments, the linker region includes an unsaturated ketone.

In some embodiments, the inhibitor is configured to bind, modify, or bind and modify amyloid precursor protein. In some embodiments, the inhibitor binds/modifies amyloid precursor protein covalently, non-covalently, or combinations thereof. In some embodiments, the inhibitor binds/modifies amyloid precursor protein at a transmembrane domain thereof. In some embodiments, the inhibitor binds/modifies amyloid precursor protein adjacent the transmembrane domain, e.g., a C-terminal juxtamembrane region. In some embodiments, the inhibitor binds/modifies amyloid precursor protein at one or more lysine residues at or adjacent the transmembrane domain, as will be discussed in greater detail below.

In some embodiments, the inhibitor includes a structure according to the following Formula II:

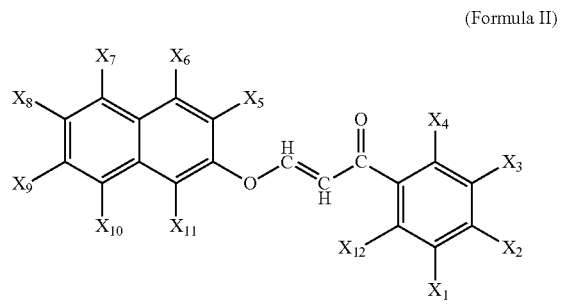

(Formula II)

In some embodiments, each of $X_1$-$X_{12}$ is one of a hydrogen, hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl group, or combinations thereof. In an exemplary embodiment, the structure includes the following Formula III:

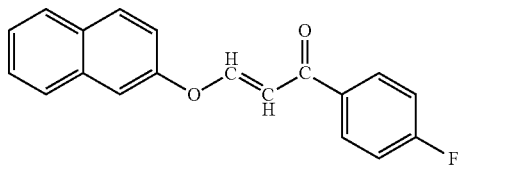

(Formula III)

In an exemplary embodiment, the structure includes the following Formula IV:

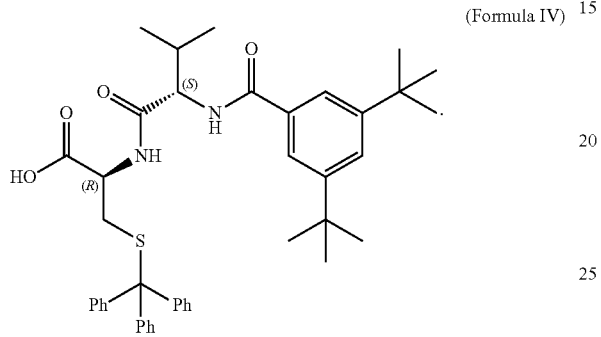

(Formula IV)

Figure 5A:
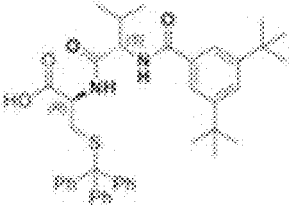
FIGS. 5A-5C is a chart of structures configured to bind to a transmembrane domain of amyloid precursor protein for use in embodiments of the present disclosure.
Figure 5A:
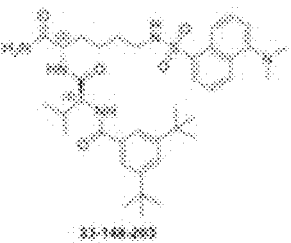
Figure 5A:
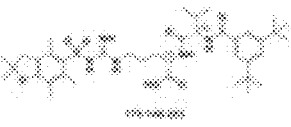
Figure 5A:
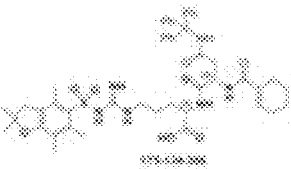
Figure 5B:
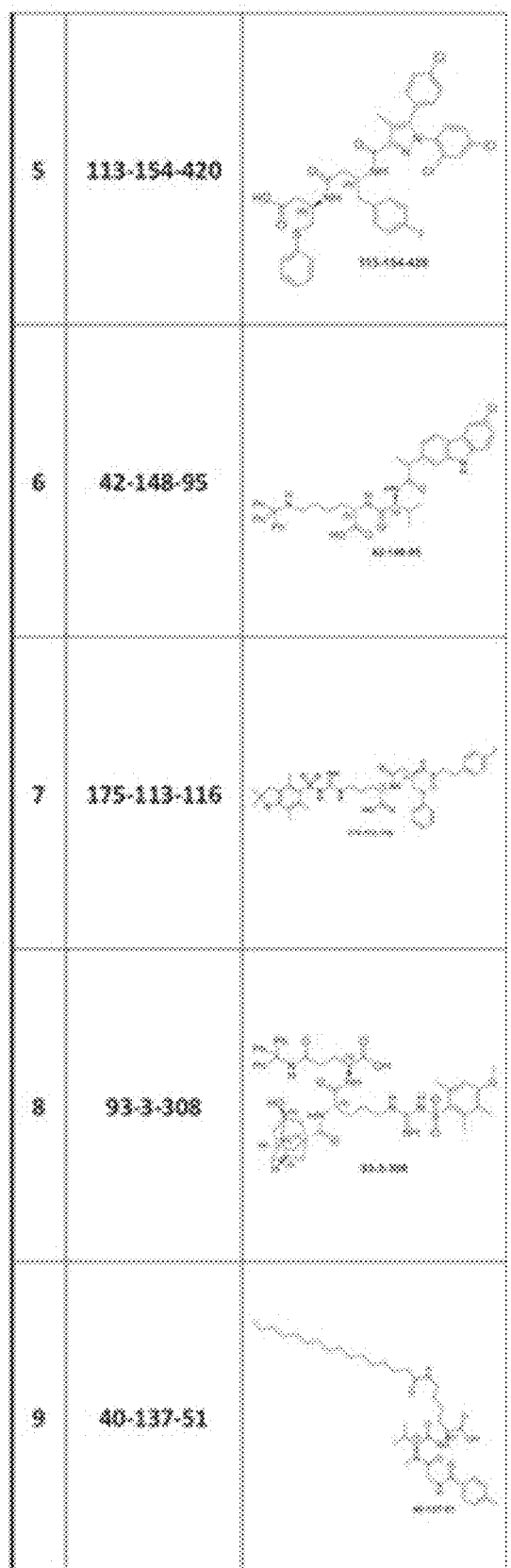
Figure 5C:
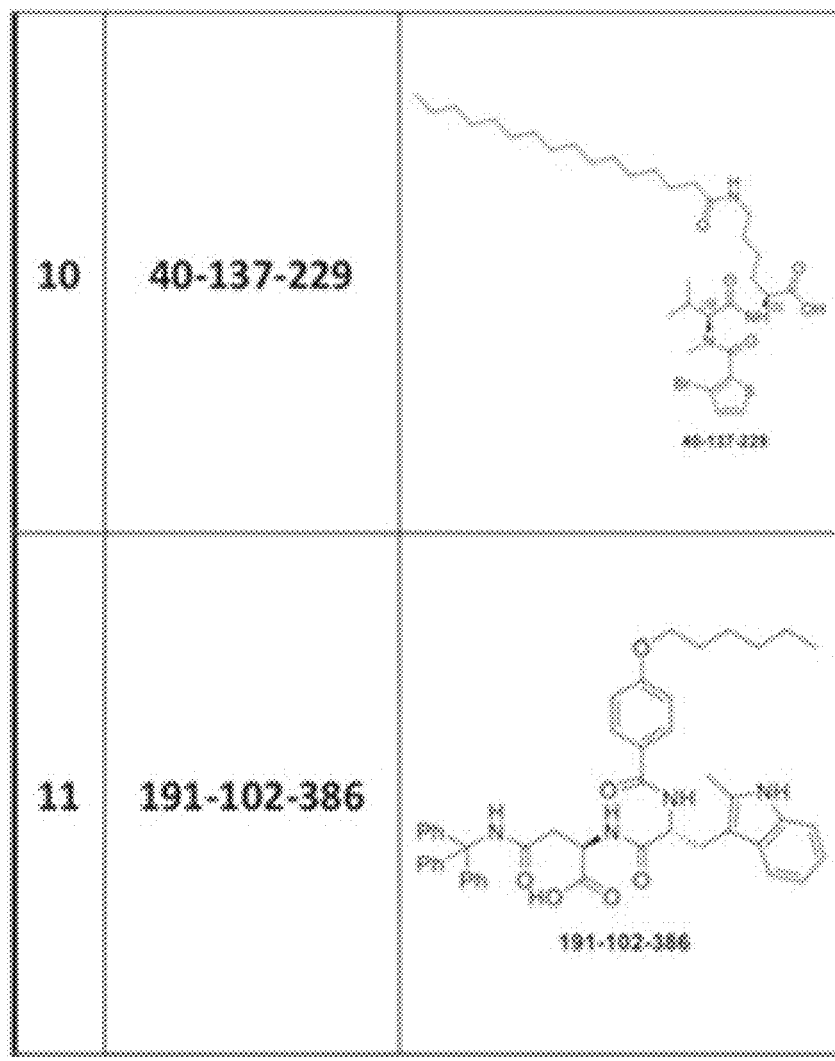

In some embodiments, the structure includes at least one of the structures identified at FIGS. 5A-5C. Referring specifically to FIG. 5C, in some embodiments, the carboxylic acid group is changed to one or more acetyl groups, e.g., to include a negative charge. In some embodiments, the chiral center is changed. In some embodiments, the aryl substitutions are changed, e.g., as removing/replacing the isobutyl group with fluorine, chlorine, —OCH$_3$, etc., or combinations thereof. In some embodiments, the tri-aryl group, the sulfur, or combinations thereof are changed.

In some embodiments, the inhibitor is incorporated into a composition for use, e.g., in vitro, in vivo, etc. In some embodiments, the inhibitor is incorporated into a composition for use as a pharmaceutical or nutraceutical. In some embodiments, the composition includes a pharmaceutically acceptable buffer, diluent, carrier, adjuvant, excipient, etc., or combinations thereof.

Figure 2:
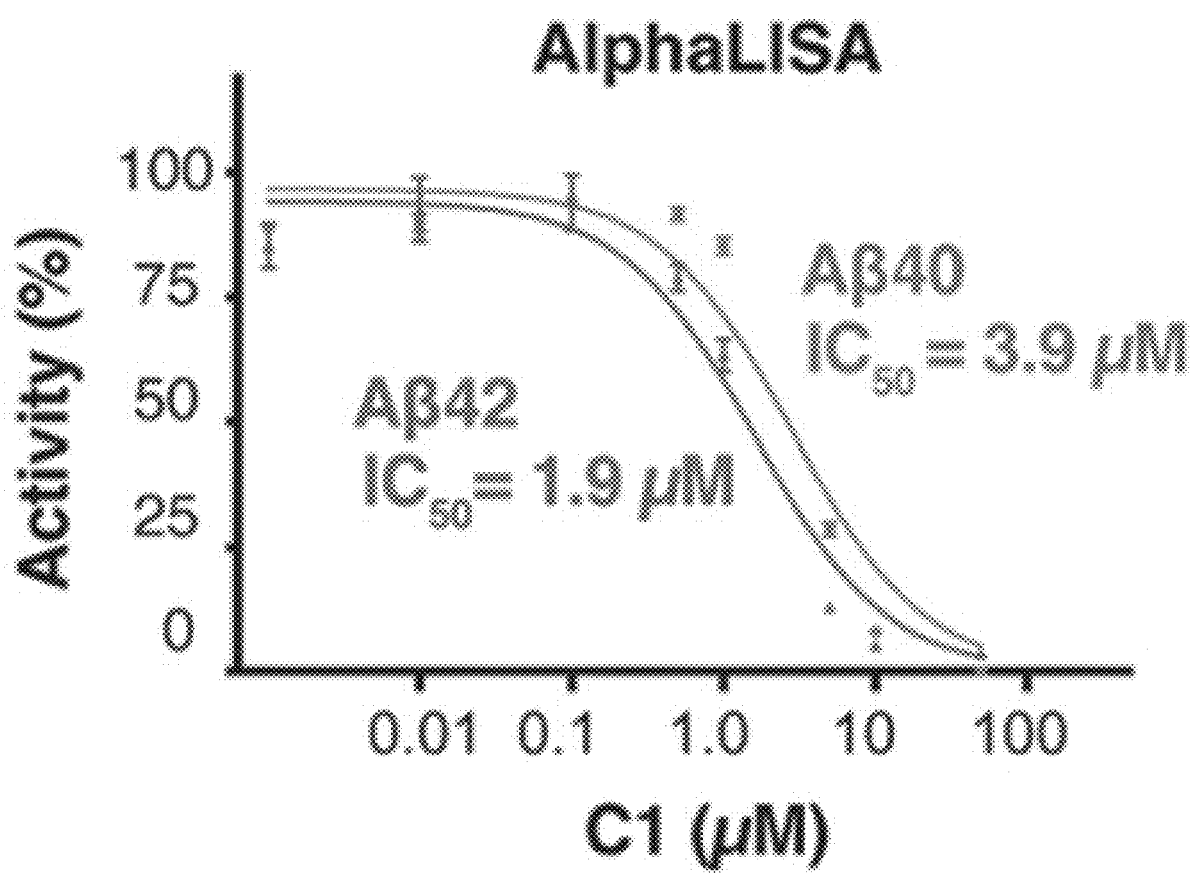
FIG. 2 is a graph portraying the activity of the γ-secretase cleavage inhibitors according to some embodiments of the present disclosure in reducing production of Aβ40 and Aβ42.

Referring now to FIG. 1, and without wishing to be bound by theory, γ-secretase cleaves within the transmembrane domain of the amyloid precursor protein (APPTM) to release Aβ, which aggregates to form neurotoxic oligomers and fibrils. To demonstrate that interaction of the inhibitory structures according to embodiments of the present disclosure and APP substrate can inhibit γ-secretase cleavage thereof, AlphaLISA assays were employed with γ-secretase in the HeLa membrane and biotinylated Sb4 based on the sequence of APP as the substrate. Formula III decreased the production of Aβ40 and Aβ42 by γ-secretase in a dose dependent manner (FIG. 2). An IC$_{50}$ value of 1.9 μM was obtained for the inhibition of Aβ42 production and 3.9 μM for the inhibition of Aβ40 production. The lower IC$_{50}$ for Aβ42 production compared to Aβ40 indicated that Formula III has selectivity in inhibiting Aβ42 production over Aβ40. Similar inhibition effects were also observed in a gel-based assay using MBP-APPTM fusion protein as the substrate and the presenilin homolog (PSH) MAMRE50 as an enzyme.

Without wishing to be bound by theory, chemical structures consistent with the present disclosure covalently modify APPTM. The α,β-unsaturated ketone in the structure is a Michael's acceptor for covalent modification of proteins. The electro-deficient β-carbon reacts with nucleophiles in proteins, such as the amino group in the side chain of lysine residues. APP includes a C-terminal juxtamembrane lysine cluster (K53, K54 and K55). Juxtamembrane residues of APP have been shown by mutagenesis to play an important role in γ-secretase cleavage, most likely through interaction with transmembrane loops in γ-secretase. The C-terminal juxtamembrane lysine cluster of APPTM is near the ε-cleavage sites T48 and L49, where initial cleavage of the protein occurs. C-terminal α-helix in APPTM unwinds into an extended β-conformation to expose the s-cleavage sites, forming an intermolecular β-sheet with two β-strands. Modification of the C-terminal juxtamembrane lysines of APPTM interferes with the α to β conformational transition and/or the formation of the intermolecular β-sheet, inhibiting γ-secretase cleavage.

Figure 3:
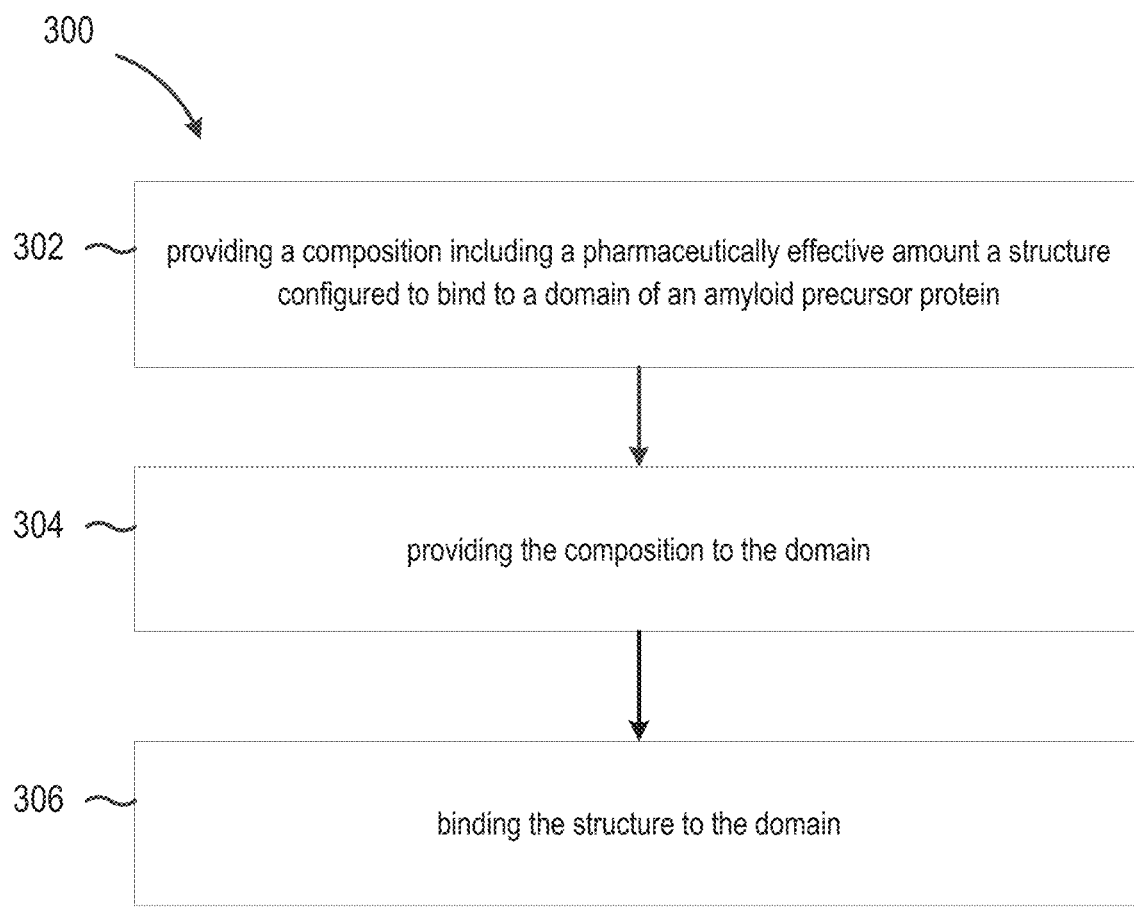
FIG. 3 is a chart of a method for inhibiting γ-secretase cleavage of amyloid precursor protein according to some embodiments of the present disclosure.

Referring now to FIG. 3, in some embodiments, the present disclosure is directed to a method 300 for inhibiting γ-secretase cleavage of amyloid precursor protein. At 302, a composition is provided. As discussed above, the composition includes a structure configured to bind to a domain of amyloid precursor protein. In some embodiments, the composition includes a pharmaceutically effective amount of the structure. In some embodiments, the pharmaceutically effective amount is sufficient to produce a localized concentration of structure of about 10 μM, 15 μM, 20 μM, or 25 μM, as will be discussed in greater detail below. In some embodiments, the composition includes a pharmaceutically acceptable buffer, diluent, carrier, adjuvant, excipient, or combinations thereof.

As discussed above, in some embodiments, the structure includes:

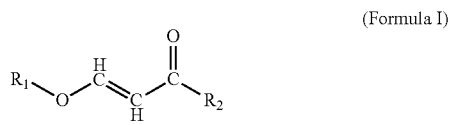

(Formula I)

In some embodiments, R$_1$ includes one or more aryl groups, heterocyclic groups, C$_{7-10}$ hydrocarbyl groups, or combinations thereof. In some embodiments, R$_2$ includes one or more aryl groups, heterocyclic groups, C$_{7-10}$ hydrocarbyl groups, or combinations thereof. In some embodiments, R$_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, R$_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, R$_1$ and R$_2$ are separated by a linker region. In some embodiments, the linker region includes an unsaturated ketone.

In some embodiments, the composition includes the structure according to the following Formula II:

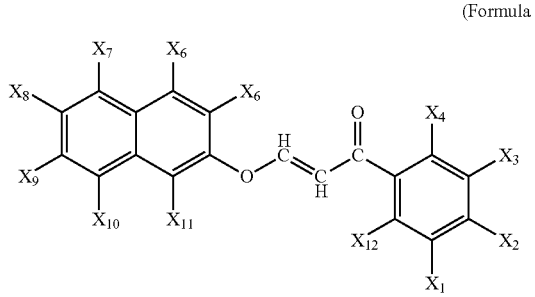

(Formula II)

In some embodiments, each of $X_1$-$X_{12}$ is one of a hydrogen, hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl group, or combinations thereof. In an exemplary embodiment, the structure includes the following Formula III:

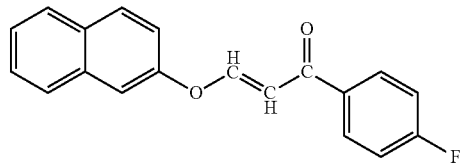

(Formula III)

In an exemplary embodiment, the structure includes the following Formula IV:

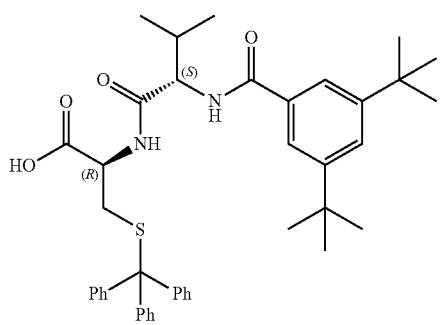

(Formula IV)

At 304, the composition is provided to amyloid precursor protein. At 306, the structure is bound to the amyloid precursor protein. In some embodiments, the structure binds/modifies amyloid precursor protein covalently, non-covalently, or combinations thereof. In some embodiments, the structure binds/modifies amyloid precursor protein at a transmembrane domain thereof, adjacent the transmembrane domain, e.g., a C-terminal juxtamembrane region, or combinations thereof. In some embodiments, the inhibitor binds/modifies amyloid precursor protein at one or more lysine residues at or adjacent the transmembrane domain, e.g., at one or more lysine residues of a C-terminal juxtamembrane region adjacent a transmembrane domain. In some embodiments, the concentration of the structure in an environment surrounding the domain after providing the composition is about 10 μM, 15 μM, 20 μM, or 25 μM.

Figure 4:
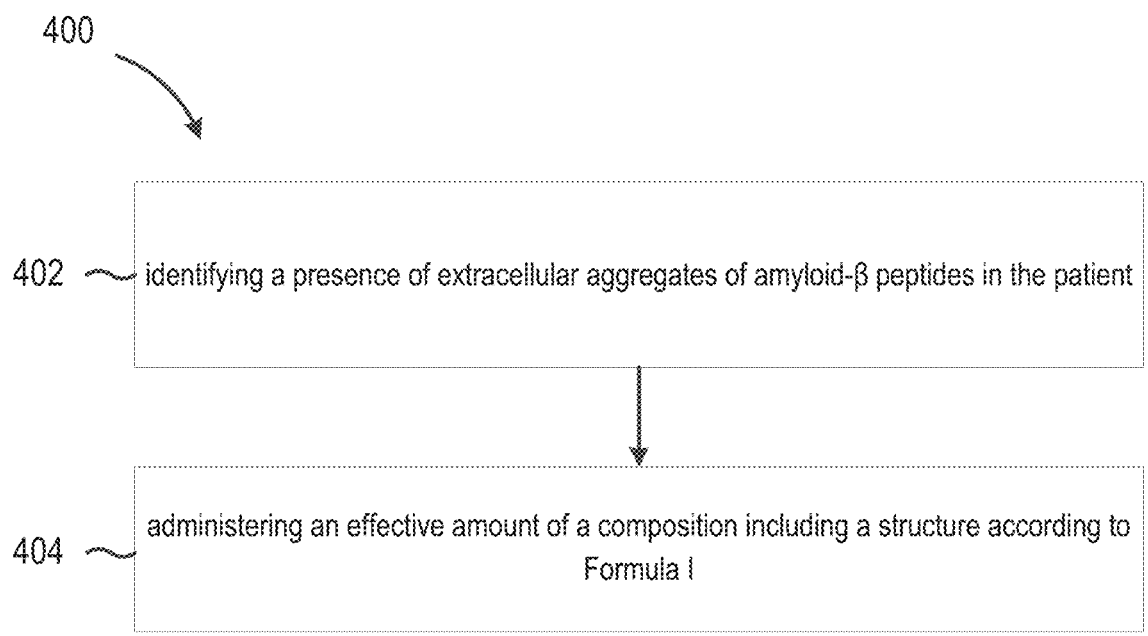
FIG. 4 is a chart of a method of reducing an amyloid load in a patient to treat a disease according to some embodiments of the present disclosure.

Referring now to FIG. 4, some embodiments of the present disclosure are directed to a method 400 of reducing an amyloid load in a patient to treat a disease. In some embodiments, the disease being treated is one resulting from or causing or believed to be resulting from or causing the buildup of amyloid plaques within the patient. In some embodiments, the disease includes Alzheimer's disease.

At 402, a presence of extracellular aggregates of amyloid-β peptides is identified in the patient. The identification of extracellular aggregates of amyloid-β peptides in the patient is performed via any suitable method, such as testing of a sample from the patient, identification of aggregates in situ, etc. At 404, a pharmaceutically effective amount of a composition including a structure configured to bind to a domain of amyloid precursor protein is administered. In some embodiments, the pharmaceutically effective amount is sufficient to produce a localized concentration of structure of about 10 μM, 15 μM, 20 μM, or 25 μM. In some embodiments, the composition includes a pharmaceutically acceptable buffer, diluent, carrier, adjuvant, excipient, or combinations thereof.

As discussed above, in some embodiments, the structure includes:

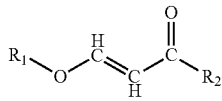

(Formula I)

In some embodiments, $R_1$ includes one or more aryl groups, heterocyclic groups, $C_{7-10}$ hydrocarbyl groups, or combinations thereof. In some embodiments, $R_2$ includes one or more aryl groups, heterocyclic groups, $C_{7-10}$ hydrocarbyl groups, or combinations thereof. In some embodiments, $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof. In some embodiments, $R_1$ and $R_2$ are separated by a linker region. In some embodiments, the linker region includes an unsaturated ketone.

In some embodiments, the composition includes the structure according to the following formula II:

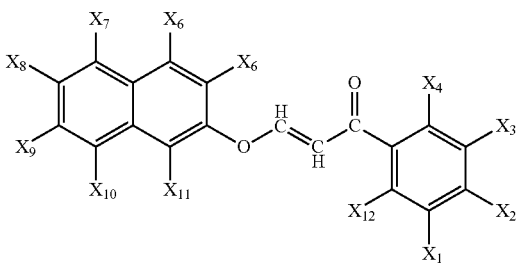

(Formula II)

In some embodiments, each of $X_1$-$X_{12}$ is one of a hydrogen, hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl group, or combinations thereof. In an exemplary embodiment, the structure includes the following Formula III:

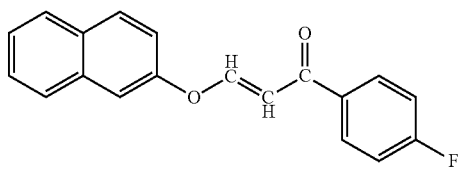

(Formula III)

In an exemplary embodiment, the structure includes the following Formula IV:

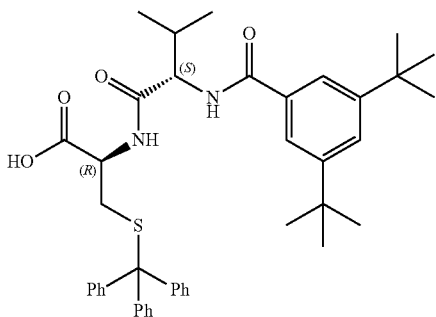

(Formula IV)

In some embodiments, the structure binds/modifies amyloid precursor protein covalently, non-covalently, or combinations thereof. In some embodiments, the structure binds/modifies amyloid precursor protein at a transmembrane domain thereof, adjacent the transmembrane domain, e.g., a C-terminal juxtamembrane region, or combinations thereof. In some embodiments, the structure binds/modifies amyloid precursor protein at one or more lysine residues at or adjacent the transmembrane domain, e.g., at one or more lysine residues of a C-terminal juxtamembrane region adjacent a transmembrane domain. As discussed above, modification of the C-terminal juxtamembrane lysines of APPTM interferes with the α to β conformational transition and/or the formation of the intermolecular β-sheet, inhibiting γ-secretase cleavage. In turn, cleavage inhibition reduces the production of Aβ40 and Aβ42, which have been shown to have a central role in the conditions including Alzheimer's disease, Down's syndrome, toxicity from Aβ aggregates, neuron inflammation, potentiation of tau pathology, etc. In some embodiments, the concentration of the structure in an environment surrounding the domain after providing the composition is about 10 μM, 15 μM, 20 μM, or 25 μM.

Methods

Figure 6:
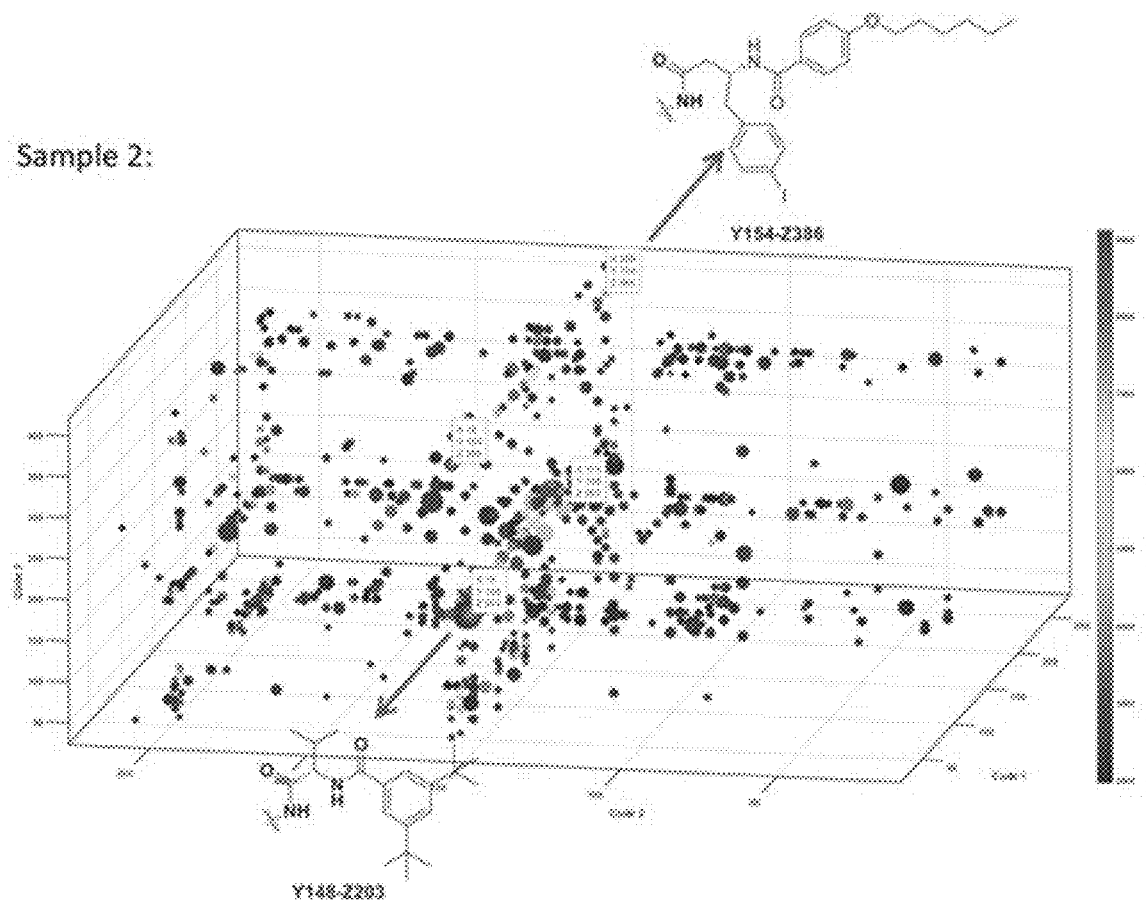
FIG. 6 is a graph portraying screening results of a DNA-encoded library (DEL) for high affinity binders to amyloid precursor protein.

Referring now to FIG. 6, a tripeptide DNA-encoded library (DEL) composed of ~20 million compounds was screened. A binding assay was carried out using Nickel-beads immobilized APPTM and DEL, PCR amplification and deep DNA sequencing. Highly-enriched compounds were then synthesized and characterized. DEL data are represented in scatter plot format. Each point represents a unique compound, with x, y, z coordinates providing the identity of the compound. The size the of the point represents fold enrichment of the compound from DEL screening compared with the initial DEL, which is a measure of the affinity between the compound and the target protein APPTM, while the color of the point encodes the number of reads in DNA deep sequencing.

Figure 7:
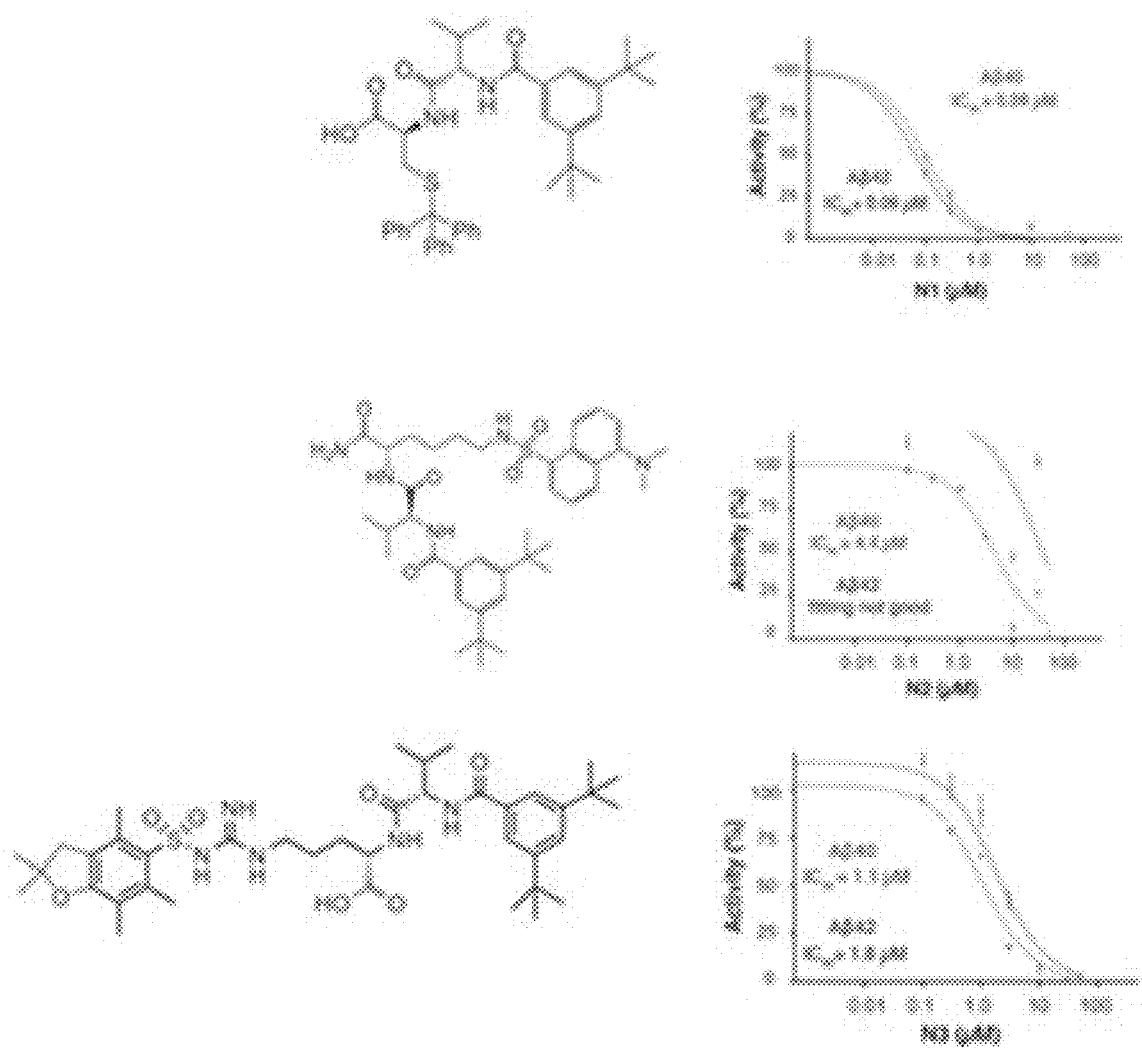
FIG. 7 portrays chemical structures identified in the DEL screening and graphs showing activity data for those structures.

Eleven compounds were synthesized in a simple, gel-based intramembrane proteolysis assay and then chose three most active compounds for AlphaLISA γ-secretase assay. These three compounds from DEL screening all showed efficacy in γ-secretase assay to various degrees (see FIG. 7), with N1 being the most potent with IC50~0.1 μM.

Figure 8A:
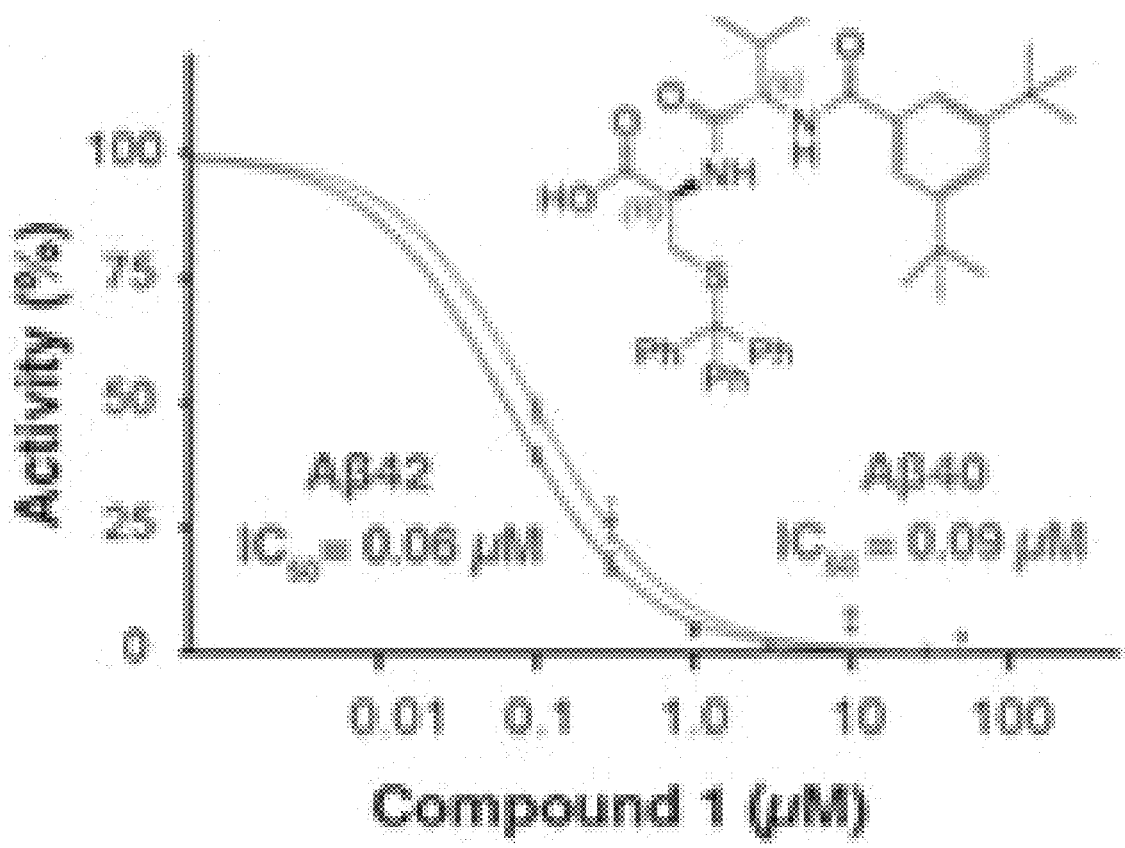
FIG. 8A portrays a graph showing the inhibitory effects of a structure for use in embodiments of the present disclosure.
Figure 8B:
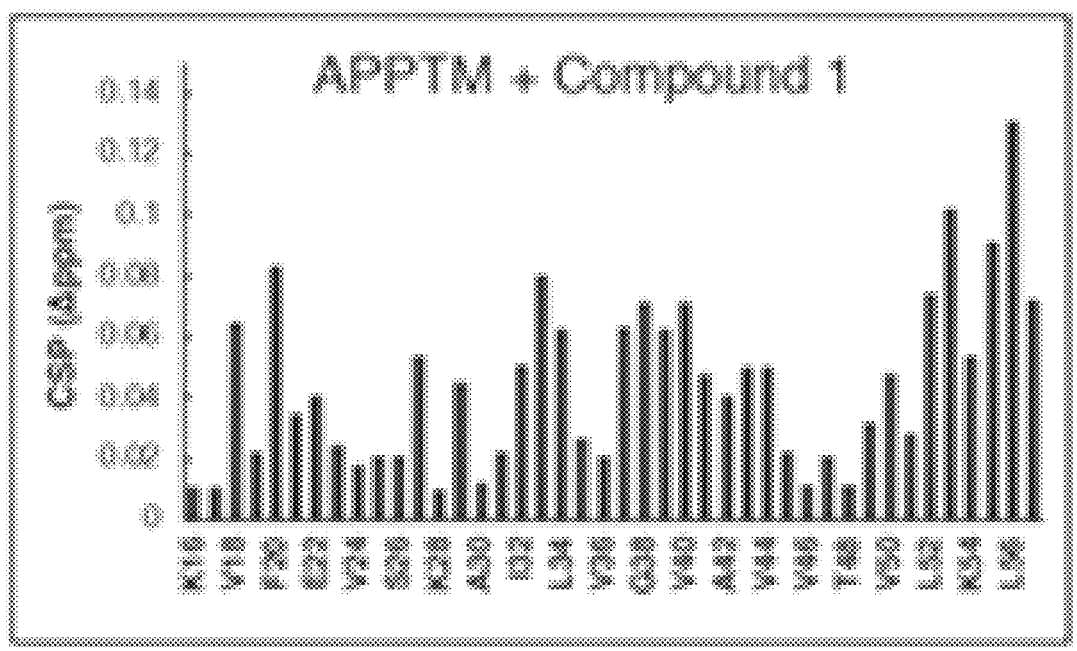
FIG. 8B is a graph showing binding of a structure for use in embodiments of the present disclosure at the C-terminal region of amyloid precursor protein.

Referring now to FIGS. 8A-8B, N1 was further characterized by NMR titration and mass spectroscopy and was found to bind non-covalently to C-terminal region of APPTM, mostly likely through electrostatic interaction with the C-terminal lysine cluster of APPTM. Compound N1 inhibits A production in AlphaLISA-secretase assay (see FIG. 8A). Further, N1 binds APPTM at the C-terminal region, non-covalently in NMR titration (see FIG. 8B).

Figure 9:
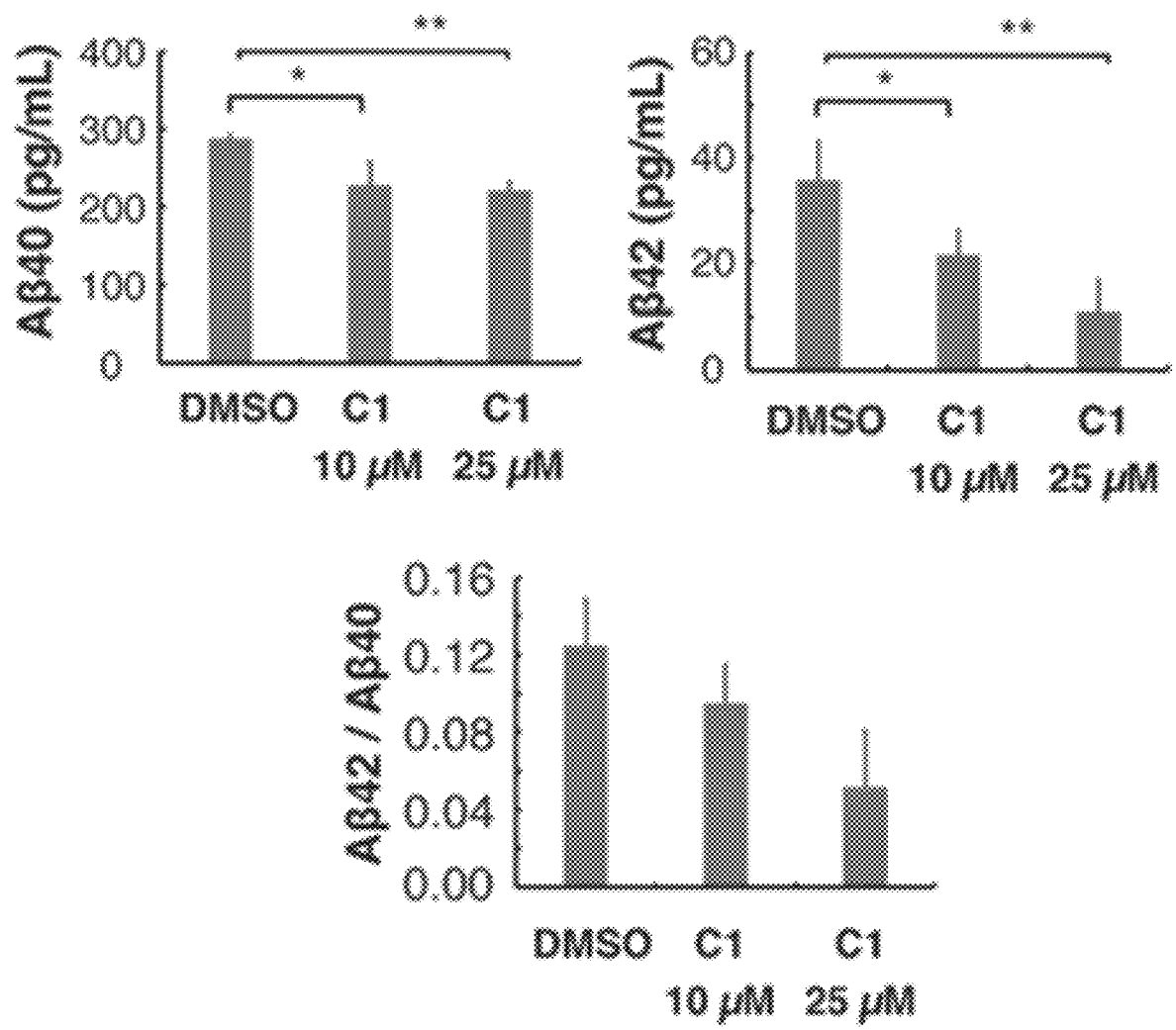
FIG. 9 is a graph portraying the activity of the γ-secretase cleavage inhibitors ("C1") according to some embodiments of the present disclosure in reducing the level of Aβ40, Aβ42 and Aβ42/Aβ40 ratio in HEK 293 cells.

The effect of the structures on Aβ40 and Aβ42 production by γ-secretase was tested in human embryonic kidney 293 (HEK 293) cells using a sandwich ELISA assay. HEK 293 cells were transfected with a plasmid to express human APP695, and Aβ40 and Aβ42 levels were measured in the conditioned medium. After the treatment by 10 μM and 25 μM of inhibitor for 24 h, the amount of Aβ40 decreased by ~25% (FIG. 9). In contrast, Aβ42 decreased by ~30% after treatment by 10 μM of the structure for 24 h, and by ~70% after treatment by 25 μM of the structure. In agreement with the AlphaLISA data, the inhibitor reduces the Aβ42 level more than that of Aβ40 in a cellular environment, reducing the Aβ42/Aβ40 ratio.

Methods and system of the present disclosure are advantageous to inhibit γ-secretase cleavage as evidenced by AlphaLISA assay, with an $IC_{50}$ of 1.9 μM for Aβ42 and 3.9 μM for Aβ40. This suggests that targeting the substrate of γ-secretase to reduce amyloid load is a viable strategy in Alzheimer's disease drug discovery. Further, the compositions of the present disclosure selectively modify APPTM in the presence of ubiquitin, showing specificity for APPTM, most likely due to its non-covalent interaction with APPTM and high reactivity of K55.

Without wishing to be bound by theory, targeting the substrate of γ-secretase alone can be sufficient for reducing Aβ production. Targeting Aβ precursor substrates of γ-secretase offers a direction in Alzheimer's disease drug discovery for reducing amyloid load as disease-modifying therapy. Furthermore, the methodology may be adapted to additional γ-secretase substrates thus enabling assessment of functional consequences of the γ-secretase cleavage of specific substrates. Further, the method inhibits Aβ production without affecting the γ-secretase activity against other non-APP substrates or presenilin function.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A method for inhibiting γ-secretase cleavage of amyloid precursor protein, comprising:
providing a composition including a pharmaceutically effective amount of a structure configured to bind to a domain of an amyloid precursor protein,
providing the composition to the domain; and
binding the structure to the domain,
wherein the structure includes:

(Formula I)

wherein $R_1$ includes one or more aryl groups, heterocyclic groups, $C_{7-10}$ hydrocarbyl groups, or combinations thereof, and $R_2$ includes one or more aryl groups, heterocyclic groups, $C_{7-10}$ hydrocarbyl groups, or combinations thereof.

2. The method according to claim 1, wherein $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof; and
$R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof.

3. The method according to claim 1, wherein the composition includes a pharmaceutically acceptable buffer, diluent, carrier, adjuvant, excipient, or combinations thereof.

4. The method according to claim 1, wherein the domain includes an amyloid precursor protein transmembrane domain, amyloid precursor protein juxtamembrane region, or combinations thereof.

5. The method according to claim 4, wherein binding the structure to the domain further comprises:
modifying one or more lysine residues of a C-terminal juxtamembrane region adjacent a transmembrane domain.

6. The method according to claim 4, wherein binding the structure to the domain includes covalent and non-covalent binding.

7. The method according to claim 1, wherein the concentration of the structure in an environment surrounding the domain after providing the composition is about 25 μM.

8. The method according to claim 1, wherein the structure includes:

(Formula III)

9. An inhibitor of γ-secretase cleavage of amyloid precursor protein, comprising:
a structure including:

(Formula I)

wherein $R_1$ includes one or more aryl groups, heterocyclic groups, $C_{7-10}$ hydrocarbyl groups, or combinations thereof, and $R_2$ includes one or more aryl groups, heterocyclic groups, $C_{7-10}$ hydrocarbyl groups, or combinations thereof.

10. The inhibitor according to claim 9, wherein $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof; and
$R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof.

11. The inhibitor according to claim 9, wherein the structure includes:

(Formula III)

12. A method of reducing an amyloid load in a patient to treat a disease, comprising:
identifying a presence of extracellular aggregates of amyloid-β peptides in the patient; and
administering an effective amount of a composition including a structure including:

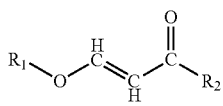

(Formula I)

wherein $R_1$ includes one or more aryl groups, heterocyclic groups, $C_{7-10}$ hydrocarbyl groups, or combinations thereof, and $R_2$ includes one or more aryl groups, heterocyclic groups, $C_{7-10}$ hydrocarbyl groups, or combinations thereof.

13. The method according to claim 12, wherein $R_1$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof; and $R_2$ is substituted with one or more functional groups including hydrocarbyl, halo, halocarbyl, hydroxy, carboxy, alkylamide, cyano, carbonyl, nitro, amino, alkylamino, thiol, mercapto, alkylthio, sulfoxide, sulfone, acyl, acylamino, amidino, aryl, haloaryl, heterocyclic, naphthyl, benzyl, aryloxy, benzyloxy, heteroaryloxy, or benzoyl groups, or combinations thereof.

14. The method according to claim 12, wherein the composition includes a pharmaceutically acceptable buffer, diluent, carrier, adjuvant, excipient, or combinations thereof.

15. The method according to claim 12, further comprising:

binding the structure to a domain of an amyloid precursor protein,
wherein the domain includes an amyloid precursor protein transmembrane domain, amyloid precursor protein juxtamembrane region, or combinations thereof.

16. The method according to claim 15, wherein binding the structure to the domain further comprises:

modifying one or more lysine residues of a C-terminal juxtamembrane region adjacent a transmembrane domain.

17. The method according to claim 15, wherein binding the structure to the domain includes covalent and non-covalent binding.

18. The method according to claim 12, wherein the concentration of the structure in an environment surrounding the domain of amyloid precursor protein after providing the composition is about 25 μM.

19. The method according to claim 12, wherein the disease is Alzheimer's disease.

20. The method according to claim 12, wherein the structure includes:

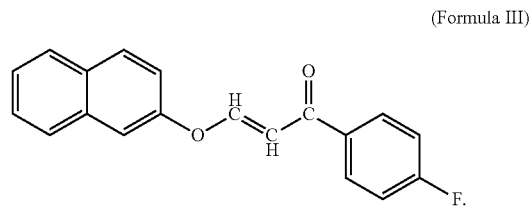 [SMILES: O=C(/C=C/Oc1ccc2ccccc2c1)c1ccc(F)cc1]

(Formula III)

* * * * *